(12) United States Patent
Walk et al.

(10) Patent No.: US 8,391,441 B2
(45) Date of Patent: Mar. 5, 2013

(54) METHOD FOR ESTIMATING A RADIATION DOSE OF AN X-RAY

(75) Inventors: Johannes Walk, Buckenhof (DE); Marcel Wellnitz, Heßdorf (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 13/204,411

(22) Filed: Aug. 5, 2011

(65) Prior Publication Data

US 2012/0195408 A1 Aug. 2, 2012

(30) Foreign Application Priority Data

Aug. 6, 2010 (DE) .......................... 10 2010 033 609

(51) Int. Cl.
*H05G 1/38* (2006.01)
(52) U.S. Cl. ............................................ 378/96; 378/97
(58) Field of Classification Search ..................... 378/96, 378/97
See application file for complete search history.

(56) References Cited

U.S. PATENT DOCUMENTS

| | | | |
|---|---|---|---|
| 2006/0067474 A1* | 3/2006 | Schmitt .................. | 378/102 |
| 2006/0233304 A1* | 10/2006 | Bernhardt et al. ............ | 378/97 |
| 2012/0138811 A1* | 6/2012 | Takenaka et al. ............ | 250/394 |

FOREIGN PATENT DOCUMENTS

| | | |
|---|---|---|
| DE | 232 592 A1 | 1/1986 |
| DE | 10 2004 048 215 A1 | 4/2006 |
| DE | 10 2005 017 489 A1 | 10/2006 |
| DE | 10 2006 037 740 A1 | 2/2008 |

OTHER PUBLICATIONS

German Office Action dated Mar. 16, 2011 for corresponding German Patent Application No. DE 10 2010 033 609.2-52 with English translation.

* cited by examiner

*Primary Examiner* — Glen Kao
(74) *Attorney, Agent, or Firm* — Lempia Summerfield Katz LLC

(57) ABSTRACT

The present embodiments specify a method and an associated X-ray facility for estimating a radiation dose of an X-ray that is generated by an X-ray source and penetrates an object under examination. First dose values of the X-ray are determined by measurement in an automatic exposure control chamber. A second dose value is determined by estimating the radiation dose that is emitted by an X-ray source in a dead time of the automatic exposure control chamber. The estimated radiation dose is determined by the first dose value and the second dose value last determined being added. The second dose value represents a correction value for a non-measurable dose during the dead time of the automatic exposure control chamber that is taken into account when determining the estimated radiation dose.

7 Claims, 3 Drawing Sheets

US 8,391,441 B2

METHOD FOR ESTIMATING A RADIATION DOSE OF AN X-RAY

This application claims the benefit of DE 10 2010 033 609.2, filed on Aug. 6, 2010.

BACKGROUND

The present embodiments relate to a method for estimating a radiation dose of an X-ray generated by an X-ray source not initially detected penetrating an object under examination.

An X-ray imaging chain may be used in X-ray systems for medical diagnostics of a human body in order to visualize processes within the body. In such cases, the X-ray imaging chain generates X-ray images that serve as a basis for diagnosis. When an X-ray is recorded, an exposure dose is measured and controlled, for example, via a radiation measurement chamber. The radiation measurement chamber may be an Automatic Exposure Control (AEC) chamber. The dose is determined in the form of an analog voltage corresponding to dose power or a digital value over a time integral. The dose is determined in the analog case on the basis of an impulse value generation with simultaneous counting. The dose is determined in the digital case by using a digital automatic exposure control chamber on the basis of an upwardly integrated counter value.

DE 10 2006 037 740 describes an X-ray diagnosis device for creating a series of X-ray images with a high-voltage generator for an X-ray emitter and with an X-ray detector. Disposed in front of the X-ray detector is a dose measurement chamber, to which measurement electronics are connected in a first control circuit that creates an actual AEC signal. An imaging system is connected via a second control circuit. The dose is determined from the image content via a component of the imaging system, and an actual dose signal is subsequently generated. During the recording of a series of X-ray images, the actual AEC signal and the actual dose signal are fed to a combined control electronics, via which the high-voltage generator may be controlled.

A basic characteristic of automatic exposure control chambers is a dose power-dependent time delay that causes the switch off to take place correspondingly later than planned. This time delay is also known as dose lag time or dead time. The dead time ranges between 300 µs and around 1 ms, for example, depending on the dose power. The disadvantage of the X-ray diagnosis device described is that, in the event of very short recording times (e.g., 1-5 ms), errors resulting from the dead time of the automatic exposure control chamber lie in the unacceptable two-digit percentage range, and optimum irradiation of an object to be examined may not be guaranteed.

SUMMARY AND DESCRIPTION

The present embodiments may obviate one or more of the drawbacks or limitations in the related art. For example, an improved method for estimating a radiation dose, generated by an X-ray source, of an X-ray penetrating an object under examination and an associated improved X-ray facility may be provided.

In one embodiment, a method for estimating a radiation dose of an X-ray that is generated by an X-ray source and penetrates an object under examination is provided. In the method, first dose values of the X-ray are determined by measurement in an automatic exposure control chamber. A second dose value is determined by estimating the radiation dose that is emitted by the X-ray source and attenuated by the object in the beam path during a dead time of the automatic exposure control chamber. The estimated radiation dose is determined by a last determined first dose value and also the second dose value being added. The second dose value represents a correction value for a non-measurable dose during the dead time of the automatic exposure control chamber, which is taken into consideration in the determination of the estimated radiation dose. The advantage of this is that the accuracy of the estimation of the radiation dose penetrating the object under examination is significantly enhanced.

The dead time describes a period of time, in which no radiation dose or only an inadequate radiation dose is determinable by the automatic exposure control chamber. This time delay is a basic characteristic of dose measurement chambers.

In one embodiment, the second dose value may be determined from a time change of the first dose values. The first dose values growing over time are determined at different points in time. After each newly-detected first dose value, the second dose value is determined from a change over time of the first dose values. The advantage of this is that, with each further first dose value detected, the accuracy of the determined second dose value is dynamically increased.

The second dose value may be determined from a gradient in the change of the first dose values over time (e.g., from the gradients of the first dose values). After each newly recorded first dose value, the second dose value is determined by calculating a steepness of the individual signals for the first dose value (e.g., via the gradients of the first dose values).

In another embodiment, the slope of the change over time of the first dose values (e.g., the gradient of the first dose values) may be determined by interpolation of the first dose values. After each newly-recorded first dose value, the change over time of the first dose values (e.g., the gradient of the first dose values) is determined by applying known mathematical interpolation methods of any given order.

The present embodiments also include an X-ray system with an automatic exposure control chamber for executing the method for estimating a radiation dose of an X-ray.

DETAILED DESCRIPTION OF THE DRAWINGS

Figure 1:
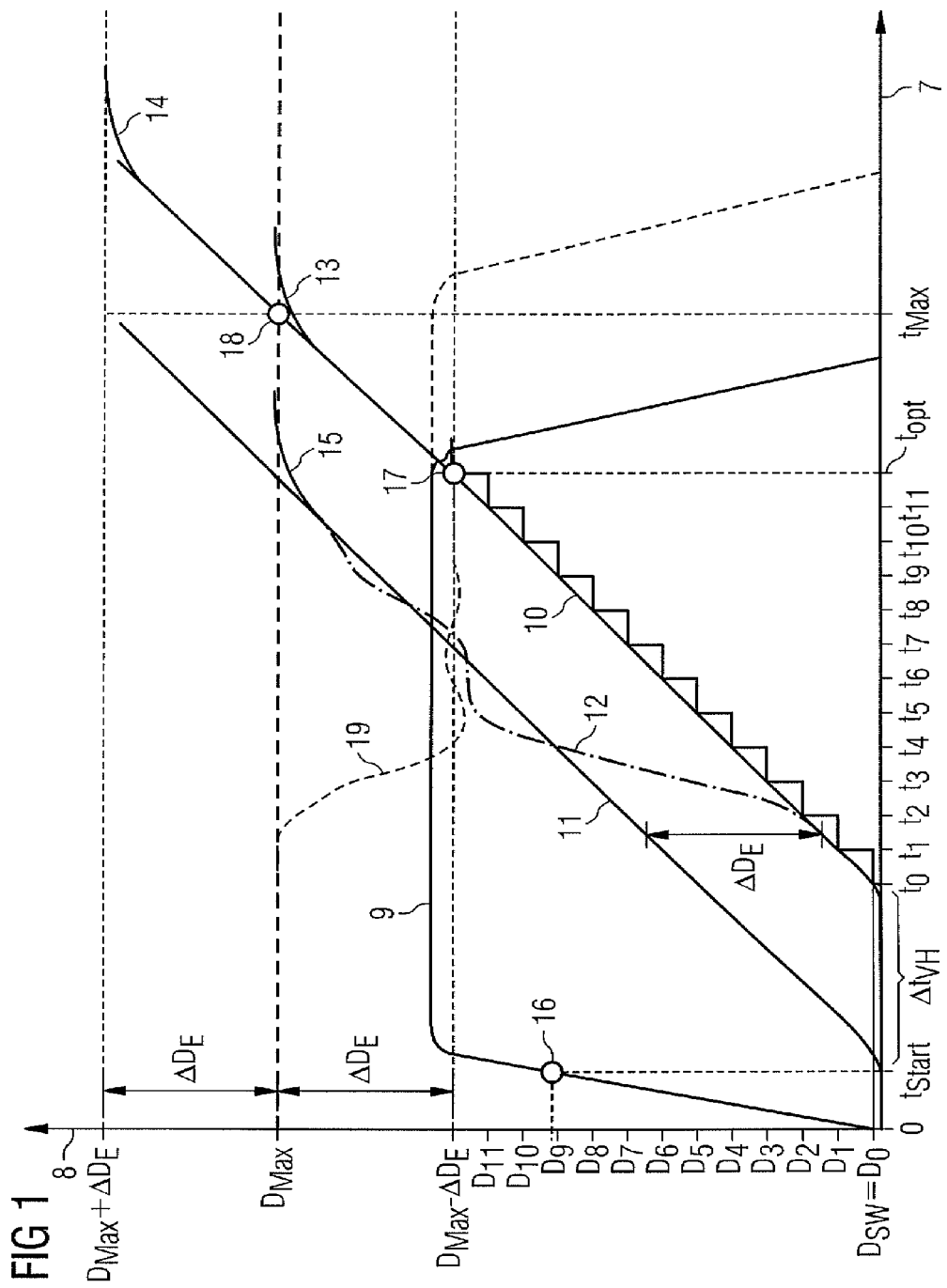
FIG. 1 shows a diagram for determining first dose values and a second dose value over time.

FIG. 1 shows a diagram for determining first dose values and a second dose value over time in an X-ray facility or system (e.g., an X-ray device). The graph in FIG. 1 shows time plotted on the x-axis 7. Shown on the y-axis 8 are detected dose values, and the development of an applied X-ray voltage 9 over the course of time is also depicted. At times $t_1 \ldots t_{11}$, measurements are taken with an automatic exposure control chamber in order to measure the first dose values $D_1 \ldots D_{11}$ of an X-ray generated by an X-ray source. At time t=0, an X-ray voltage 9 is applied by the X-ray source. Time $t_{Start}$ identifies a start time of an X-ray voltage effective for irradiation. This occurs in an automatic exposure control chamber. An associated radiation dose 16 is not measurable because of the fast buildup of the high-voltage. A time interval from $t_{Start}$ until a first point in time $t_0$ represents a dead time $\Delta t_{VH}$ of the automatic exposure control chamber. A mathematical interpolation is carried out over the first dose values $D_1 \ldots D_{11}$ for pairs of values $(t_1,D_1) \ldots (t_{11},D_{11})$ and an interpolation curve 10 is determined. By shifting the interpolation curve 10 into the point in time $t_{Start}$, resulting in an interpolation curve 11, a second dose value $\Delta D_E$ is determined. The second dose value $\Delta D_E$ gives an estimation of a radiation dose in the dead time $\Delta t_{VH}$ of the automatic exposure control chamber.

Dose value $D_{Max}$ describes a maximum dose value predeterminable for an X-ray recording. An optimum time $t_{opt}$ for switching off the voltage of the X-ray source is determined via the second dose value $\Delta D_E$ determined. The optimum time $t_{opt}$ is determined from the time at which the interpolation curve 10 assumes value $(D_{Max}-\Delta DE)$. The associated dose value is identified by reference character 17. The shape of curve 13 during time $[t_{opt}; t_{max}]$ corresponds to the course of the radiation dose as a result of the dead time $\Delta t_{VH}$, which is given by time interval $[t_{start};t_0]$. Curve shape 15 reflects the course of the radiation dose with lag-corrected switch-off.

Curves 12 and 19 show the course of lag-corrected and dose-corrected curves 13 with $D_{max}$ as an upper limit, as is approached during the estimation. As a contrasting example, curve shape 14 shows the course of the radiation dose when the radiation is switched off without taking account of the dead time $\Delta t_{VH}$ at time $t_{Max}$. The resulting overall dose in this case is $(D_{Max}+\Delta D_E)$. The associated dose value is identified by reference character 18. The overall dose 18 is achieved by known methods.

Figure 2:
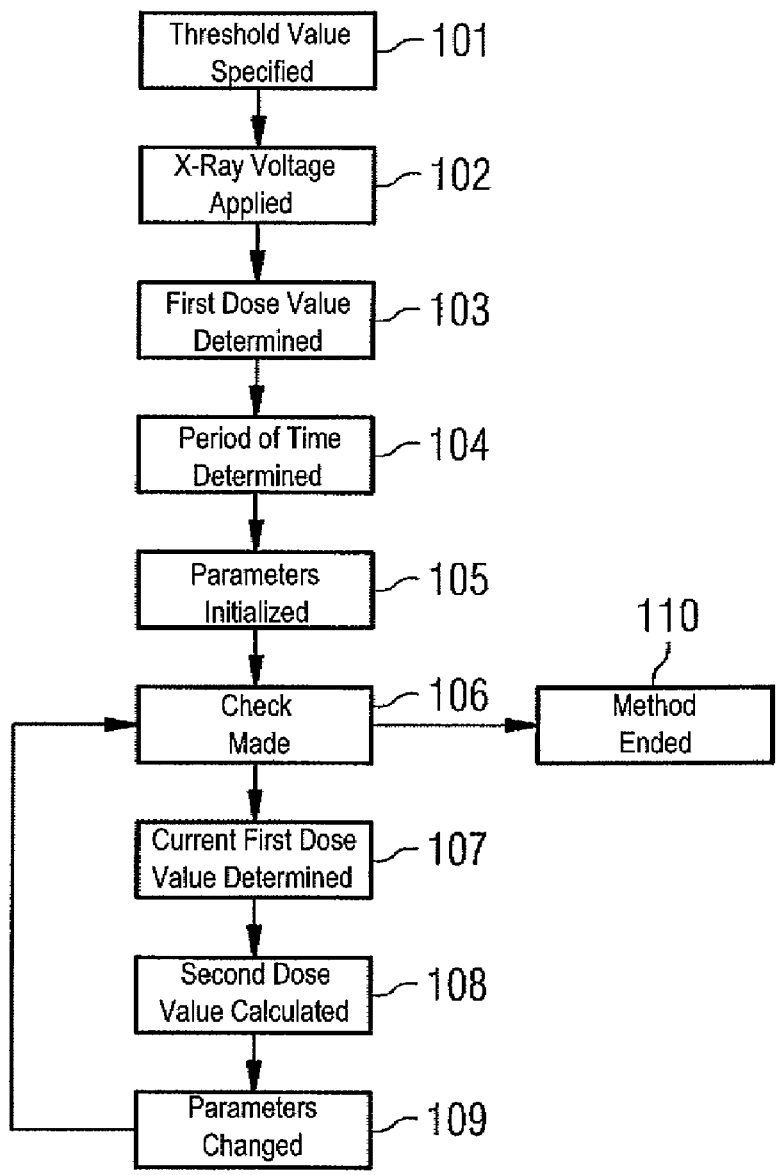
FIG. 2 shows a flow diagram of one embodiment of a method for determining a second dose value.

FIG. 2 shows a flow diagram of a method for determining a second dose value. In method act 101, a threshold value $D_{SW}$ for detecting the dose of a first dose value $D_i$ is specified. In act 102, an X-ray voltage is applied, and a timer is started. An elapsed time $t_{T1}$ is measured via a first timer $T_1$. Simultaneously, a second timer $T_2$ is set to a predeterminable limit time $t_{T2}$, in which lag dose estimation is to take place. The predeterminable limit time $t_{T2}$ specifies maximum activity for lag correction. After the predeterminable time limit $t_{T2}$ has elapsed, which is far greater than the lag time, the algorithm is deactivated, since error caused by the lag no longer plays any role. This predeterminable time limit $t_{T2}$ may be 100 ms to 255 ms, for example. The second timer $T_2$ runs back to 0 after the second timer $T_2$ is started.

In act 103, a first dose value is determined until a time when a value of the first dose value exceeds the dose threshold value $D_{SW}$. Subsequently, the time recorded by the first timer $T_1$ is stopped. In act 104, the period of time determined by the first timer $T_1$ is divided by a value 8, and the result is allocated to the constant $\tau$. The constant $\tau$ specifies a waiting time between two consecutive measurements of the first dose value $D_i$ and $D_{i+1}$.

In act 105, parameters i and j, by which iterations of the algorithm are controlled, are initialized with the value 1. $D_0$ is set as the last measured first dose value. The first timer $T_1$ is also set to the value $\tau$ and started. The first timer $T_1$ runs backwards to 0. In method act 106, a check is first made as to whether the second timer $T_2$ has timed out. If the second timer $T_2$ has timed out, the method is ended with act 110. If the second timer $T_2$ has not timed out, the process waits for the length of time $t_{T1}$.

In act 107, the current first dose value $D_i$ is determined. At the same time, the first timer $T_1$ is set to $\tau$ and started. In act 108, the second dose value $\Delta D_E$ is calculated using the following specification:

$$\text{for } i<15: \quad j=i \text{ and } \Delta D_E = \left(\sum_{n=0}^{j}\left(\frac{(D_{(n+1)}-D_{(n)})}{j+1}\right)\right)*8$$

$$\text{for } i>=15: \quad j=15 \text{ and } \Delta D_E = \left(\sum_{n=(i-j)}^{i}\left(\frac{(D_{(n+1)}-D_{(n)})}{j+1}\right)\right)*8$$

In act 109, the run parameter i is changed as a function of the value of the parameter j in accordance with the following specification:
for i<15: i:=i+1;
for i≧15: i:=0.
The parameter j is changed in accordance with the following specification:
for j<15: j:=j+1;
for j≧15: j=15.
Subsequently, the procedure branches back to act 106.

Figure 3:
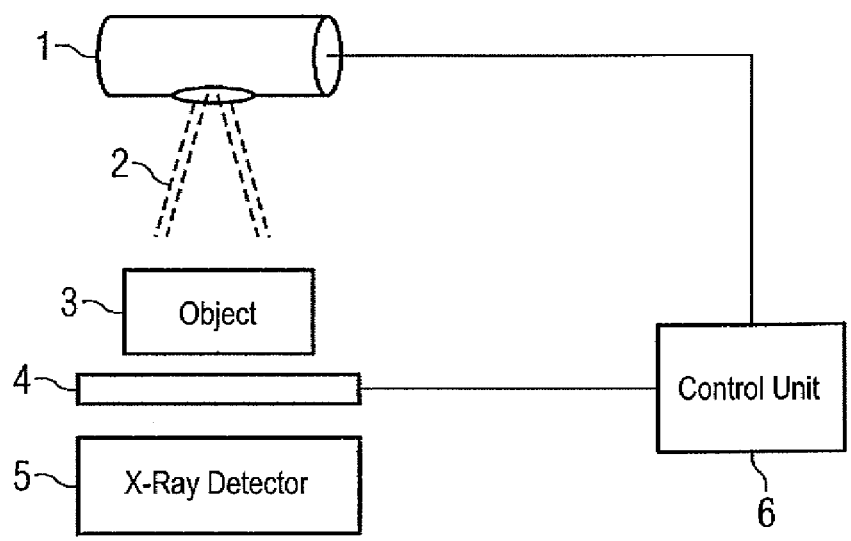
FIG. 3 shows a block diagram of one embodiment of an X-ray system for estimating a radiation dose of an X-ray.

FIG. 3 shows a block diagram of an X-ray facility or system for estimating a radiation dose of an X-ray. A conical bundled X-ray 2 is generated via an X-ray source 1. The conical bundled X-ray 2 penetrates an object under examination 3 located in a beam path of the X-ray 2. Arranged downstream in the beam path is an automatic exposure control chamber 4, via which the radiation dose is measured. An X-ray detector 5 detects the X-ray 2. The automatic exposure control chamber 4 is connected to a control unit 6 and transfers the first dose values determined by the automatic exposure control chamber 4 to the control unit 6 via this connection. In the control unit 6, a second dose value is determined by estimating a radiation dose emitted by the X-ray source 1 in a dead time of the automatic exposure control chamber 4. The estimated radiation dose is determined in the control unit 6 by summation of the last first radiation dose value determined and the second dose value. The control unit 6 is connected to the X-ray source 1 and controls the radiation dose emitted by the X-ray source 1 via this interface.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for estimating a radiation dose of an X-ray penetrating an object under examination, the X-ray being generated by an X-ray source, the method comprising:
   determining first dose values of the X-ray by measurement in an automatic exposure control chamber;
   determining a second dose value by estimating a radiation dose emitted in a dead time of the automatic exposure control chamber by the X-ray source; and
   determining the estimated radiation dose by summation of the last determined first dose value and the second dose value.

2. The method as claimed in claim 1, wherein no radiation dose or only an inadequate radiation dose is determinable by the automatic exposure control chamber in the dead time.

3. The method as claimed in claim 2, wherein the second dose value is determined from a change of the first dose values over time.

4. The method as claimed in claim 1, wherein the second dose value is determined from a change of the first dose values over time.

5. The method as claimed in claim 4, wherein the second dose value is determined from a gradient of the change of the first dose values over time.

6. The method as claimed in claim 5, wherein the gradient is determined by interpolation of the first dose values.

7. An x-ray system comprising:
- an x-ray source operable to generate an x-ray beam;
- an automatic exposure control chamber configured to estimate a radiation dose of an X-ray penetrating an object under examination, the automatic exposure control chamber configured to:
  - determine first dose values of the X-ray by measurement in the automatic exposure control chamber;
  - determine a second dose value by estimating a radiation dose emitted in a dead time of the automatic exposure control chamber by the X-ray source; and
  - determine the estimated radiation dose by summation of the last determined first dose value and the second dose value.

* * * * *